United States Patent
Weser et al.

(10) Patent No.: US 9,839,596 B2
(45) Date of Patent: Dec. 12, 2017

(54) OXIDATION DYE WITH REDUCED HAIR DAMAGE

(71) Applicant: Henkel AG & Co. KGaA, Duesseldorf (DE)

(72) Inventors: Gabriele Weser, Neuss (DE); Ulrike Schumacher, Duesseldorf (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/184,729

(22) Filed: Jun. 16, 2016

(65) Prior Publication Data

US 2016/0296452 A1 Oct. 13, 2016

Related U.S. Application Data

(63) Continuation of application No. PCT/EP2014/074968, filed on Nov. 19, 2014.

(30) Foreign Application Priority Data

Dec. 19, 2013 (DE) .................. 10 2013 226 587

(51) Int. Cl.
*A61Q 5/10* (2006.01)
*A61K 8/73* (2006.01)
*A61Q 5/08* (2006.01)
*A61K 8/04* (2006.01)

(52) U.S. Cl.
CPC ............... *A61K 8/73* (2013.01); *A61K 8/042* (2013.01); *A61Q 5/08* (2013.01); *A61Q 5/10* (2013.01); *A61K 2800/4324* (2013.01); *A61K 2800/882* (2013.01); *A61K 2800/884* (2013.01)

(58) Field of Classification Search
CPC . A61Q 5/08; A61Q 5/10; A61K 8/042; A61K 8/73; A61K 2800/884; A61K 2800/4324; A61K 2800/882
See application file for complete search history.

(56) References Cited

U.S. PATENT DOCUMENTS

| 6,190,647 B1 * | 2/2001 | Karlen ................. A61K 8/8152 132/202 |
| 2002/0010970 A1 * | 1/2002 | Cottard .................. A61K 8/342 8/405 |

FOREIGN PATENT DOCUMENTS

| EP | 0962218 A2 | 12/1999 |
| EP | 2345400 A2 | 7/2011 |
| WO | 2013/013863 A2 | 1/2013 |
| WO | 2013/069166 A1 | 5/2013 |
| WO | 2013/069168 A1 | 5/2013 |

OTHER PUBLICATIONS

PCT International Search Report (PCT/EP2014/074968) dated Feb. 25, 2015.

* cited by examiner

*Primary Examiner* — Eisa Elhilo
(74) *Attorney, Agent, or Firm* — P. Scott Smith

(57) ABSTRACT

An oxidation dye and/or lightener, which is in the form of a preferably transparent hydrogel, has a pH value in the range of 7.0 to 8.8, and preferably after being mixed with an acidic oxidizing agent preparation produces an application mixture having a pH value in the range of 6.0 to 7.3, makes possible intensive coloring or lightening of fibers with reduced hair damage.

13 Claims, No Drawings

OXIDATION DYE WITH REDUCED HAIR DAMAGE

FIELD OF THE INVENTION

The present invention generally relates to oxidation dyes and/or lighteners for keratinic fibers, which are associated with reduced hair damage compared with conventional oxidation dyes. The present invention, furthermore, relates to a corresponding kit for the oxidative dyeing or lightening of keratin-containing fibers and to a coloring and/or lightening method for keratinic fibers with the aid of the agents of the invention.

BACKGROUND OF THE INVENTION

So-called oxidation dyes are used for permanent, intensive colors with suitable fastness properties. Oxidation dyes typically consist of two components: one component typically includes oxidation dye precursors, so-called developer components and coupler components. The developer components form the actual dyes under the effect of oxidizing agents, in particular hydrogen peroxide, which are added to the first components only shortly before the application to hair, or of atmospheric oxygen with one another or with coupling with one or more coupler components. Primary aromatic amines with a further free or substituted hydroxy or amino group, in the para or ortho position, diaminopyridine derivatives, heterocyclic hydrazones, 4-aminopyrazolone derivatives and 2,4,5,6-tetraaminopyrimidine, and derivatives thereof are usually used as developer components. M-Phenylenediamine derivatives, naphthols, resorcinol, and resorcinol derivatives, pyrazolones, m-aminophenols, and substituted pyridine derivatives are normally used as coupler components. The oxidation dyes are characterized by excellent, long-lasting coloring results.

In order to stabilize the dye precursors during storage and to accelerate the reaction during the oxidative application, conventional oxidation dyes have a higher alkaline pH, which is far above 9.0 and is adjusted with alkalizing agents, such as alkanolamines, ammonia, or inorganic bases. Although in this regard ammonia in particular enables good coloring results, it also manifests disadvantages for the user due to its odor and irritation potential for skin and mucous membranes. The alkalizing agent results in the swelling of the keratinic fibers, as a result of which the dye precursors can easily penetrate into the hair. Nevertheless, the damaging action of the oxidizing agent on the hair structure is also intensified by the alkaline pH. For this reason, particular efforts focus on developing high-performance oxidation dyes, which have as low a pH as possible, therefore requiring only a low content of alkalizing agents, so that the damage to the hair structure by the oxidizing agent can be minimized.

Commercial oxidation dyes, in particular those sold at retail and used by the customer at home, are typically provided with standard directions for use, which recommend a specific application time for which the dye is to remain on the hair. This application time was determined by the manufacturer in extensive tests involving volunteers and is more likely based on subjects who have hair that is difficult to color or lighten and in whom the color absorbs onto the hair only after a rather long treatment time or the desired degree of lightening is achieved after a longer treatment time. Consumers with hair that is easy to color accordingly could definitely shorten the recommended standard application time and nevertheless achieve a good coloring or lightening result. In order to reduce the damage to the hair structure still further, it would be desirable therefore to limit the application time to the time after which the desired hair color was achieved. In order to realize this, it would be beneficial for the coloring component, as well as the application mixture, therefore the mixture of the color component and oxidizing agent, to be transparent.

Another requirement for oxidation dyes and/or lighteners is that the application mixture of the dye components and oxidizing agent component is sufficiently viscous, so that they can applied conveniently to hair and can remain there for the entire application time without any dripping or running.

The object of the present invention therefore was to provide oxidation dyes and/or lighteners for keratinic fibers, in particular hair, which cause as little hair damage as possible, in particular with good dyeing and/or lightening results, comparable to conventional highly alkaline dyes, and in particular with good absorption of the dyes on the keratinic fibers. A further object of the present invention was to provide transparent oxidation dyes and/or lighteners.

It was found surprisingly that oxidation dyes and/or lighteners, which are preferably transparent hydrogels and have a pH in the range of 7.0 to 8.8 and which preferably after mixing with an acidic oxidizing agent preparation produce an application mixture with a pH in the range of 6.0 to 7.3, enable intensive dyeing or lightening of the fibers, and nevertheless are associated with reduced hair damage.

Furthermore, other desirable features and characteristics of the present invention will become apparent from the subsequent detailed description of the invention and the appended claims, taken in conjunction with this background of the invention.

BRIEF SUMMARY OF THE INVENTION

An agent for dyeing and/or lightening keratinic fibers, including: 80-93 wt. %, based on the agent, of water or a mixture of water and at least one water-soluble polyol, whereby at least 30 wt. % of water, based on the agent, is present; furthermore at least one hydrogel-forming polymer, selected from the group formed by polysaccharides, polymers and copolymers of acrylic acid, polymers and copolymers of methacrylic acid, and polymers and copolymers of 2-methyl-2[(1-oxo-2-propenyl)amino]-1-propanesulfonic acid, and of mixtures thereof, furthermore at least one alkalizing agent; furthermore at least one solubilizer, selected from fatty alcohol glycol ethers, fatty alcohols, fatty acid glycerol esters, and fatty acid sorbitan esters, each of which is ethoxylated and optionally propoxylated; optionally at least one oxidation dye precursor and/or at least one direct dye; whereby the agent has a pH in the range of 7.0 to 8.8, measured at 22° C.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A first subject matter of the present invention is an agent for dyeing and/or lightening of keratinic fibers, including 80-93 wt. %, based on the agent, of water or a mixture of water and at least one water-soluble polyol, whereby at least 30 wt. % of water, based on the agent, is present, furthermore at least one hydrogel-forming polymer, selected from the group formed by polysaccharides, polymers and copolymers of acrylic acid, polymers and copolymers of methacrylic acid, and polymers and copolymers of 2-methyl-2[(1-oxo-2-propenyl)amino]-1-propanesulfonic acid, and of mixtures thereof, furthermore at least one alkalizing agent, furthermore at least one solubilizer, selected from fatty alcohol glycol ethers, fatty alcohols, fatty acid glycerol esters, and fatty acid sorbitan esters, each of which is ethoxylated and optionally propoxylated, optionally at least one oxidation dye precursor and/or at least one direct dye, whereby the agent has a pH in the range of 7.0 to 8.8, measured at 22° C.

The agents of the invention are present as hydrogels and accordingly include 80-93 wt. % of an aqueous carrier, which consists either solely of water or, however, of a mixture of water and at least one water-soluble polyol, whereby at least 30 wt. % of water, based on the agent, is present, however.

According to the invention, a water-soluble polyol is understood to be a polyol with a solubility of at least 5 wt. % at 20° C., in other words, that at least 5 g of the polyol is soluble in 95 g of water at 20° C.

Preferred water-soluble polyols are selected from at least one water-soluble polyhydric $C_2$-$C_9$ alkanol with 2-6 hydroxyl groups and/or at least one water-soluble polyethylene glycol with 3-20 ethylene oxide units, and mixtures thereof. Preferably, these polyols are selected from 1,2-propylene glycol, 1,3-propylene glycol, 2-methyl-1,3-propanediol, glycerol, 1,2-butylene glycol, 1,3-butylene glycol, 1,4-butylene glycol, 1,2-pentanediol, 1,5-pentanediol, 1,2-hexanediol, 1,6-hexanediol, 2-methyl-2,4-pentanediol, 1,2,6-hexanetriol, 1,2-octanediol, 1,8-octanediol, dipropylene glycol, tripropylene glycol, diglycerol, triglycerol, erythritol, sorbitol, cis-1,4-dimethylolcyclohexane, trans-1,4-dimethylolcyclohexane, any isomer mixtures of cis- and trans-1,4-dimethylolcyclohexane, PEG-3, PEG-4, PEG-6, PEG-7, PEG-8, PEG-9, PEG-10, PEG-12, PEG-14, PEG-16, PEG-18, and PEG-20, and mixtures thereof. Particularly preferred water-soluble polyols are selected from 1,2-propylene glycol, glycerol, 1,3-butylene glycol, 1,6-hexanediol, dipropylene glycol, and PEG-8, and mixtures thereof. 1,2-Propylene glycol is exceedingly preferred.

The at least one water-soluble polyol is preferably used in a total amount of 0.5-63 wt. %, particularly preferably in a total amount of 1-50 wt. %, more particularly preferably in a total amount of 2-30 wt. %, and exceedingly preferably in a total amount of 4-10 wt. %, based in each case on the weight of the agent of the invention.

The agents of the invention include as a second component, essential to the invention, at least one hydrogel-forming polymer, selected from the group formed by polysaccharides, polymers and copolymers of acrylic acid, polymers and copolymers of methacrylic acid, and polymers and copolymers of 2-methyl-2[(1-oxo-2-propenyl)amino]-1-propanesulfonic acid, and of mixtures thereof.

Polymers are understood to be macromolecules with a molecular weight of at least 1000 g/mol, preferably of at least 2500 g/mol, particularly preferably of at least 5000 g/mol, which consist of the same repeating organic units. Polymers are prepared by polymerization of a monomer type or by polymerization of various structurally different monomer types. If the polymer is prepared by polymerization of a monomer type, the term homopolymers is used. If structurally different monomer types are used in the polymerization, the skilled artisan uses the term copolymers. The maximum molecular weight of the polymer depends on the degree of polymerization (number of polymerized monomers) and is also determined by the polymerization method. In the context of the present invention, it is preferable if the molecular weight of the employed polymers is 100,000 to $10^7$ g/mol, preferably 200,000 to $5\cdot10^6$ g/mol, and particularly preferably 500,000 to $1\cdot10^6$ g/mol.

Preferred agents of the invention are characterized in that the at least one polysaccharide is selected from xanthan gum, cellulose, cellulose ethers, primarily hydroxyalkyl celluloses, in particular hydroxypropyl cellulose, hydroxypropyl methylcellulose, hydroxyethyl cellulose, carboxymethyl cellulose, hydroxybutyl methyl cellulose, methyl hydroxyethyl cellulose, sclerotium gum, succinoglucans, polygalactomannans, in particular guar-gums and locust bean gum, in particular guar-gum and locust bean gum themselves and nonionic hydroxyalkyl guar derivatives and locust bean gum derivatives, such as hydroxypropyl guar, carboxymethyl hydroxypropyl guar, hydroxypropylmethyl guar, hydroxyethyl guar, and carboxymethyl guar, furthermore pectins, agar, kappa-carrageenan, iota-carrageenan, tragacanth, gum arabic, karaya gum, tara gum, gellan gum, gelatin, casein, propylene glycol alginate, alginic acids and salts thereof, in particular sodium alginate, potassium alginate, and calcium alginate, and mixtures thereof. Particularly preferred polysaccharides are selected from xanthan gum, cellulose, cellulose ethers, primarily hydroxyalkyl celluloses, in particular hydroxypropyl cellulose, hydroxypropyl methylcellulose, hydroxyethyl cellulose, carboxymethyl cellulose, hydroxybutyl methyl cellulose, methyl hydroxyethyl cellulose, and mixtures thereof. Xanthan gum is exceedingly preferred.

Preferred agents of the invention are characterized in that at least one hydrogel-forming polymer is selected from at least one polymer or copolymer of acrylic acid and/or methacrylic acid and/or 2-methyl-2[(1-oxo-2-propenyl)amino]-1-propanesulfonic acid, preferably selected from crosslinked homopolymers of acrylic acid, crosslinked homopolymers of 2-methyl-2 [(1-oxo-2-propenyl)amino]-1-propanesulfonic acid, crosslinked copolymers of methacrylic acid and C1-C4 alkyl acrylates, crosslinked copolymers of acrylic acid and C1-C4 alkyl methacrylates, crosslinked copolymers of 2-methyl-2[(1-oxo-2-propenyl)amino]-1-propanesulfonic acid and acrylamide, crosslinked copolymers of 2-methyl-2[(1-oxo-2-propenyl)amino]-1-propanesulfonic acid and vinylpyrrolidone, crosslinked copolymers of 2-methyl-2 [(1-oxo-2-propenyl)amino]-1-propanesulfonic acid and 2-hydroxyethyl acrylate, crosslinked copolymers of 2-methyl-2[(1-oxo-2-propenyl) amino]-1-propanesulfonic acid and acrylic acid, crosslinked copolymers of acrylic acid and C10-30 alkyl acrylates, crosslinked terpolymers and quaterpolymers of 2-methyl-2 [(1-oxo-2-propenyl)amino]-1-propanesulfonic acid or acrylic acid or methacrylic acid, and mixtures of said polymers.

Preferably, the at least one hydrogel-forming polymer is selected from crosslinked homopolymers of acrylic acid, in particular those with the INCI name Carbomer, and crosslinked copolymers of methacrylic acid and C1-C4 alkyl acrylates.

Particularly preferred agents of the invention are characterized in that they include at least one polysaccharide, which is selected from xanthan gum, cellulose, cellulose ethers, primarily hydroxyalkyl celluloses, in particular hydroxypropyl cellulose, hydroxypropyl methylcellulose, hydroxyethyl cellulose, carboxymethyl cellulose, hydroxybutyl methyl cellulose, methyl hydroxyethyl cellulose, sclerotium gum, succinoglucans, polygalactomannans, in particular guar-gums and locust bean gum, in particular guar-gum and locust bean gum themselves and nonionic hydroxyalkyl guar derivatives and locust bean gum derivatives, such as hydroxypropyl guar, carboxymethyl hydroxypropyl guar, hydroxypropylmethyl guar, hydroxyethyl guar, and carboxymethyl guar, furthermore pectins, agar, kappa-carrageenan, iota-carrageenan, tragacanth, gum arabic, karaya gum, tara gum, gellan gum, gelatin, casein, propylene glycol alginate, alginic acids and salts thereof, in particular sodium alginate, potassium alginate, and calcium alginate, and mixtures thereof, and at least one polymer, selected from at least one polymer or copolymer of acrylic acid and/or methacrylic acid and/or 2-methyl-2[(1-oxo-2-propenyl)amino]-1-propanesulfonic acid.

Other particularly preferred agents of the invention are characterized in that they include at least one polysaccharide, selected from xanthan gum, cellulose, cellulose ethers, primarily hydroxyalkyl celluloses, in particular hydroxypropyl cellulose, hydroxypropyl methylcellulose, hydroxyethyl cellulose, carboxymethyl cellulose, hydroxybutyl methyl cellulose, methylhydroxy ethyl cellulose, sclerotium gum, succinoglucans, polygalactomannans, in particular guar-gums and locust bean gum, in particular guar-gum and locust bean gum themselves and nonionic hydroxyalkyl guar derivatives and locust bean gum derivatives, such as hydroxypropyl guar, carboxymethyl hydroxypropyl guar, hydroxypropylmethyl guar, hydroxyethyl guar, and carboxymethyl guar, furthermore pectins, agar, kappa-carrageenan, iota-carrageenan, tragacanth, gum arabic, karaya gum, tara gum, gellan gum, gelatin, casein, propylene glycol alginate, alginic acids and salts thereof, in particular sodium alginate, potassium alginate, and calcium alginate, and mixtures thereof, and at least one polymer, selected from crosslinked homopolymers of acrylic acid, crosslinked homopolymers of 2-methyl-2[(1-oxo-2-propenyl)amino]-1-propanesulfonic acid, crosslinked copolymers of methacrylic acid and C1-C4 alkyl acrylates, crosslinked copolymers of acrylic acid and C1-C4 alkyl methacrylates, crosslinked copolymers of 2-methyl-2[(1-oxo-2-propenyl)amino]-1-propanesulfonic acid and acrylamide, crosslinked copolymers of 2-methyl-2[(1-oxo-2-propenyl)amino]-1-propanesulfonic acid and vinylpyrrolidone, crosslinked copolymers of 2-methyl-2[(1-oxo-2-propenyl)amino]-1-propanesulfonic acid and 2-hydroxyethyl acrylate, crosslinked copolymers of 2-methyl-2[(1-oxo-2-propenyl)amino]-1-propanesulfonic acid and acrylic acid, crosslinked copolymers of acrylic acid and C10-30 alkyl acrylates, crosslinked terpolymers and quaterpolymers of 2-methyl-2 [(1-oxo-2-propenyl)amino]-1-propanesulfonic acid or acrylic acid or methacrylic acid, and mixtures of said polymers.

Other particularly preferred agents of the invention are characterized in that they include xanthan gum and at least one crosslinked acrylic acid homopolymer.

The at least one polysaccharide, selected from xanthan gum, cellulose, cellulose ethers, primarily hydroxyalkyl celluloses, in particular hydroxypropyl cellulose, hydroxypropyl methylcellulose, hydroxyethyl cellulose, carboxymethyl cellulose, hydroxybutyl methyl cellulose, methylhydroxy ethyl cellulose, sclerotium gum, succinoglucans, polygalactomannans, in particular guar-gums and locust bean gum, in particular guar-gum and locust bean gum themselves and nonionic hydroxyalkyl guar derivatives and locust bean gum derivatives, such as hydroxypropyl guar, carboxymethyl hydroxypropyl guar, hydroxypropylmethyl guar, hydroxyethyl guar, and carboxymethyl guar, furthermore pectins, agar, kappa-carrageenan, iota-carrageenan, tragacanth, gum arabic, karaya gum, tara gum, gellan gum, gelatin, casein, propylene glycol alginate, alginic acids and salts thereof, in particular sodium alginate, potassium alginate, and calcium alginate, and mixtures thereof, is preferably present in a total amount of 0.2 to 3 wt. %, particularly preferably 0.5-2 wt. %, and exceedingly preferably 0.8 to 1.5 wt. %, based in each case on the weight of the agent of the invention.

The at least one polymer or copolymer of acrylic acid and/or methacrylic acid and/or 2-methyl-2[(1-oxo-2-propenyl)amino]-1-propanesulfonic acid, is preferably present in a total amount of 0.2 to 3 wt. %, particularly preferably 0.5-2 wt. %, and exceedingly preferably 0.8 to 1.5 wt. %, based in each case on the weight of the agent of the invention.

The at least one polymer or copolymer, selected from crosslinked homopolymers of acrylic acid, crosslinked homopolymers of 2-methyl-2[(1-oxo-2-propenyl)amino]-1-propanesulfonic acid, crosslinked copolymers of methacrylic acid and C1-C4 alkyl acrylates, crosslinked copolymers of acrylic acid and C1-C4 alkyl methacrylates, crosslinked copolymers of 2-methyl-2[(1-oxo-2-propenyl) amino]-1-propanesulfonic acid and acrylamide, crosslinked copolymers of 2-methyl-2[(1-oxo-2-propenyl)amino]-1-propanesulfonic acid and vinylpyrrolidone, crosslinked copolymers of 2-methyl-2[(1-oxo-2-propenyl)amino]-1-propanesulfonic acid and 2-hydroxyethyl acrylate, crosslinked copolymers of 2-methyl-2[(1-oxo-2-propenyl) amino]-1-propanesulfonic acid and acrylic acid, crosslinked copolymers of acrylic acid and C10-30 alkyl acrylates, crosslinked terpolymers and quaterpolymers of 2-methyl-2 [(1-oxo-2-propenyl)amino]-1-propanesulfonic acid or acrylic acid or methacrylic acid, and mixtures of said polymers, is preferably present in a total amount of 0.2 to 3 wt. %, particularly preferably 0.5-2 wt. %, and exceedingly preferably 0.8 to 1.5 wt. %, based in each case on the weight of the agent of the invention.

Other particularly preferred agents of the invention are characterized in that they include 0.2 to 3 wt. %, particularly preferably 0.5-2 wt. %, and exceedingly preferably 0.8 to 1.5 wt. % of xanthan gum, and at least one crosslinked acrylic acid homopolymer in a total amount of 0.2 to 3 wt. %, particularly preferably 0.5-2 wt. %, and exceedingly preferably 0.8 to 1.5 wt. %, based in each case on the weight of the agent of the invention.

The agents of the invention include at least one alkalizing agent as a third component essential to the invention. Preferably, the alkalizing agent is selected from ammonia and at least one alkanolamine. Alkanolamines preferred according to the invention are selected from alkanolamines from primary, secondary, or tertiary amines with a $C_2$-$C_6$ alkyl parent structure, bearing at least one hydroxyl group. Particularly preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methylpropanol, 2-amino-2-methylbutanol, 3-amino-2-methylpropan-1-ol, 1-amino-2-methylpropan-2-ol, 3-aminopropane-1,2-diol, 2-amino-2-methylpropane-1,3-diol, 2-amino-2-ethyl-1,3-propanediol, N,N-dimethylethanolamine, triethanolamine, diethanolamine, and triisopropanolamine. Alkanolamines very particularly preferred according to the invention are selected from the group comprising 2-aminoethan-1-ol (monoethanolamine), 2-amino-2-methylpropan-1-ol, 2-amino-2-methylpropane-1,3-diol, and triethanolamine. Particularly preferred agents include monoethanolamine as the alkanolamine. Preferably, the at least one alkanolamine is present in a total amount of 0.05 to 10 wt. %, in particular of 0.5 to 6 wt. %, and particularly preferably 1-3 wt. %, based in each case on the weight of the agent of the invention.

Other alkalizing agents preferred according to the invention are selected from inorganic alkalizing agents. Ammonia, likewise an inorganic alkalizing agent, is nevertheless less preferable, because it can volatilize too early during use. Preferred agents of the invention and application mixtures therefore contain, based in each case on their weight, 0 to 0.5 wt. %, preferably zero wt. % of ammonia.

Preferred inorganic alkalizing agents are selected from the group formed by sodium hydroxide, potassium hydroxide, calcium hydroxide, barium hydroxide, sodium phosphate, potassium phosphate, sodium silicate, potassium silicate, sodium carbonate, and potassium carbonate, and mixtures thereof. Other alkalizing agents preferred according to the invention are selected from basic amino acids, particularly preferably selected from the group formed by L-arginine, D-arginine, D/L-arginine, L-lysine, D-lysine, D/L-lysine, and mixtures thereof. Basic amino acids particularly preferred according to the invention are selected from L-arginine, D-arginine, and D/L-arginine. Preferred agents of the invention include at least one alkalizing agent different from alkanolamines and ammonia in a total amount of 0.05 to 5 wt. %, in particular of 0.5 to 3 wt. %, based in each case on the weight of the agent.

Care must be taken in determining the optimal amount of alkalizing agent that the agent of the invention has a pH in the range of 7.0 to 8.8, preferably in the range of 7.5 to 8.5, in each case measured at 22° C.

As a fourth component essential to the invention, the agents of the invention include at least one solubilizer, selected from fatty alcohol glycol ethers, fatty alcohols, and fatty acid glycerol esters, each of which is ethoxylated and optionally propoxylated.

Fatty alcohols are understood to be preferably $C_8$-$C_{24}$ alkanols, which may be linear or branched and unsaturated or saturated. Typical examples are capryl alcohol, capric alcohol, undecyl alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol, and natural fatty alcohols, such as coconut alcohol.

Fatty acids are understood to be preferably $C_8$-$C_{24}$ alkanoic acids, which may be linear or branched and unsaturated or saturated. Typical examples are capric acid, lauric acid, myristic acid, palmitic acid, palmitoleic acid, stearic acid, isostearic acid, oleic acid, elaidic acid, petroselinic acid, linoleic acid, linolenic acid, arachidic acid, gadoleic acid, behenic acid, or erucic acid, and natural fatty acids such as coconut fatty acids.

Agents preferred according the invention include at least one solubilizer, which is selected from ethoxylated $C_8$-$C_{24}$ alkanols with 9-100 mol of ethylene oxide per mole, $C_8$-$C_{24}$ alkyl epoxide-ethylene glycol adducts, which are ethoxylated with 5-20 mol of ethylene oxide per mole and propoxylated with 1 mol of propylene oxide per mole, with 9-100 mol of ethylene oxide per mole of ethoxylated glycerol monoesters, diesters, or triesters of linear saturated and unsaturated $C_{12}$-$C_{30}$ carboxylic acids, which may be hydroxylated, in particular those of myristic acid, palmitic acid, stearic acid, oleic acid, or of mixtures of said fatty acids, ethoxylated $C_8$-$C_{24}$ carboxylic acids with 9-100 mol of ethylene oxide per mole, with 9-100 mol of ethylene oxide per mole of ethoxylated fatty acid glycerol esters of linear saturated and unsaturated $C_{12}$-$C_{30}$ carboxylic acids, which may be hydroxylated, in particular those of myristic acid, palmitic acid, stearic acid, or of mixtures of said fatty acids, with 9-100 mol of ethylene oxide per mole of ethoxylated sorbitan monoesters of linear saturated and unsaturated $C_{12}$-$C_{30}$ carboxylic acids, which may be hydroxylated, in particular those of myristic acid, palmitic acid, stearic acid, or of mixtures of said fatty acids, and mixtures of the aforesaid substances.

The ethoxylated $C_8$-$C_{24}$ alkanols have the formula $R^1O(CH_2CH_2O)_nH$, where $R^1$ stands for a linear or branched alkyl and/or alkenyl group having 8-24 carbon atoms and n, the number of ethylene oxide units per molecule, for numbers from 9 to 100, preferably 9-30 mol of ethylene oxide to 1 mol of capryl alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, and brassidyl alcohol, and technical mixtures thereof. Adducts of 9-100 mol of ethylene oxide to technical fatty alcohols having 12-18 carbon atoms, such as, for example, coconut, palm, palm kernel, or tallow fatty alcohol, are suitable.

The ethoxylated $C_8$-$C_{24}$ carboxylic acids have the formula $R^2O(CH_2CH_2O)_nH$, where $R^2O$ stands for a linear or branched saturated or unsaturated acyl group having 8-24 carbon atoms and n, the average number the ethylene oxide units per molecule, for numbers from 9 to 100, preferably 10 to 30 mol of ethylene oxide to 1 mol of capryl acid, 2-ethylhexanoic acid, capric acid, lauric acid, isotridecanoic acid, myristic acid, cetylic acid, palmitoleic acid, stearic acid, isostearic acid, oleic acid, elaidic acid, petroselinic acid, arachidic acid, gadoleic acid, behenic acid, erucic acid, and brassidic acid, and technical mixtures thereof. Adducts of 9 to 100 mol of ethylene oxide to technical fatty acids having 12-18 carbon atoms, such as coconut, palm, palm kernel, or tallow fatty acid, are suitable. Particularly preferred are PEG-50 monostearate, PEG-100 monostearate, PEG-50 monooleate, PEG-100 monooleate, PEG-50 monolaurate, and PEG-100 monolaurate.

Used particularly preferably are the $C_{12}$-$C_{18}$ alkanols each with 9-30 units of ethylene oxide per molecule and mixtures of said substances, in particular Ceteth-10, Ceteth-12, Ceteth-20, Ceteth-30, Steareth-10, Steareth-12, Steareth-20, Steareth-30, Ceteareth-10, Ceteareth-12, Ceteareth-20, Ceteareth-30, Laureth-12, and Beheneth-20.

Preferred fatty acid glycerol esters, ethoxylated with 20-100 mol of ethylene oxide per mole, said esters of linear saturated and unsaturated $C_{12}$-$C_{30}$ carboxylic acids, which may be hydroxylated, are selected from PEG-40 hydrogenated castor oil, PEG-60 hydrogenated castor oil, PEG-80 hydrogenated castor oil, PEG-40 castor oil, PEG-60 castor oil, and PEG-80 castor oil, and mixtures thereof.

Preferred sorbitan monoesters, ethoxylated with 20-100 mol of ethylene oxide per mole, said monoesters of linear saturated and unsaturated $C_{12}$-$C_{30}$ carboxylic acids, which may be hydroxylated, are selected from polysorbate-20, polysorbate-40, polysorbate-60, and polysorbate-80.

Particularly preferred solubilizers are selected from fatty alcohol glycol ethers, which are ethoxylated and optionally propoxylated, in particular from the reaction products of ethylene glycol with the epoxides of capryl alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, and brassidyl alcohol, which are alkoxylated with 1-3 units of propylene oxide per molecule and 9-30 units of ethylene oxide per molecule.

An exceedingly preferred solubilizer, selected from fatty alcohol glycol ethers, each of which are ethoxylated and optionally propoxylated, is PPG-1-PEG-9 Lauryl Glycol Ether. Excellent success is achieved with this solubilizer in solubilizing the oxidation dye precursors to such an extent that a gel as transparent as possible is obtained. A sketch of the structure of PPG-1-PEG-9 Lauryl Glycol Ether is provided below. The subscripts a and c preferably stand for the value 1, and the subscripts b and d preferably stand for the value 9. A preferred PPG-1-PEG-9 Lauryl Glycol Ether is the commercial product Eumulgin L from BASF.

amount of 1 to 4 wt. %, and exceedingly preferably in a total amount of 2 to 3 wt. %, based in each case on the weight of the agent.

An exceedingly preferred agent of the invention includes 0.1 to 10 wt. %, in particular 0.5 to 5 wt. %, more preferably 1 to 4 wt. %, exceedingly preferably 2 to 3 wt. %, of PPG-1-PEG-9 Lauryl Glycol Ether, based in each case on the weight of the agent.

As stated above, preferred agents of the invention are as transparent as possible.

Other preferred agents of the invention are therefore characterized by a turbidity in the range from zero to 80 NTU (nephelometric turbidity unit), preferably of a maximum of 60 NTU, particularly preferably of a maximum of 50 NTU, exceedingly preferably of a maximum of 40 NTU, in each case measured at 22° C. according to DIN EN ISO 7027-C2.

Provided the agents of the invention are agents for permanent dyeing and optionally simultaneous bleaching of keratinic fibers, they include at least one oxidation dye precursor. Preferably, the agent includes one or more developer components and optionally one or more coupler components.

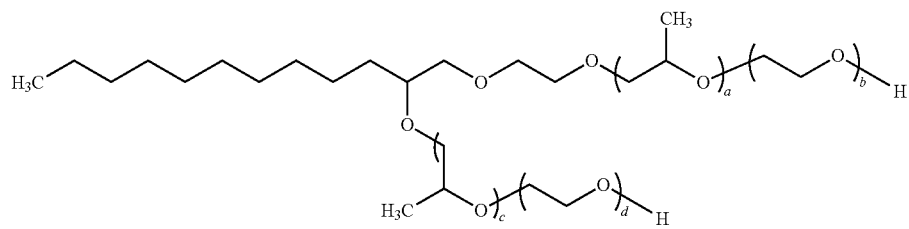

Preferred agents of the invention include at least one solubilizer, selected from fatty alcohol glycol ethers, fatty alcohols, and fatty acid glycerol esters, each of which are ethoxylated and optionally propoxylated, in a total amount of 0.1 to 10 wt. %, in particular in a total amount of 0.5 to 5 wt. %, more preferably in a total amount of 1 to 4 wt. %, and exceedingly preferably in a total amount of 2 to 3 wt. %, based in each case on the weight of the agent.

Other preferred agents of the invention include at least one solubilizer, selected from ethoxylated $C_8$-$C_{24}$ alkanols with 9-100 mol of ethylene oxide per mole, $C_8$-$C_{24}$ alkyl epoxide-ethylene glycol adducts, which are ethoxylated with 5-20 mol of ethylene oxide per mole and propoxylated with 1 mol of propylene oxide per mole, with 9-100 mol of ethylene oxide per mole of ethoxylated glycerol monoesters, diesters, or triesters of linear saturated and unsaturated $C_{12}$-$C_{30}$ carboxylic acids, which may be hydroxylated, in particular those of myristic acid, palmitic acid, stearic acid, oleic acid, or of mixtures of said fatty acids, ethoxylated $C_8$-$C_{24}$ carboxylic acids with 9-100 mol of ethylene oxide per mole, with 9-100 mol of ethylene oxide per mole of ethoxylated fatty acid glycerol esters of linear saturated and unsaturated $C_{12}$-$C_{30}$ carboxylic acids, which may be hydroxylated, in particular those of myristic acid, palmitic acid, stearic acid, or of mixtures of said fatty acids, with 9-100 mol of ethylene oxide per mole of ethoxylated sorbitan monoesters of linear saturated and unsaturated $C_{12}$-$C_{30}$ carboxylic acids, which may be hydroxylated, in particular those of myristic acid, palmitic acid, stearic acid, or of mixtures of said fatty acids, and mixtures of the aforesaid substances, in a total amount of 0.1 to 10 wt. %, in particular in a total amount of 0.5 to 5 wt. %, more preferably in a total The developer components form the actual dyes under the influence of oxidizing agents or atmospheric oxygen with one another or during coupling with one or more coupler components. Primary aromatic amines with a further free or substituted hydroxy or amino group, in the para or ortho position, diaminopyridine derivatives, heterocyclic hydrazones, 4-aminopyrazolone derivatives and 2,4,5,6-tetraaminopyrimidine, and derivatives thereof are usually used as developer components.

It can be preferred according to the invention to use a p-phenylenediamine derivative or one of the physiologically acceptable salts thereof as a developer component. Particularly preferred are the p-phenylenediamine derivatives of the formula (E1)

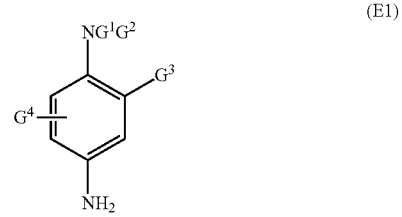

(E1)

where
$G^1$ stands for a hydrogen atom, a $C_1$-$C_4$ alkyl group, a $C_1$-$C_4$ monohydroxyalkyl group, a $C_2$-$C_4$ polyhydroxyalkyl group, a $C_1$-$C_4$-alkoxy-($C_1$-$C_4$)-alkyl group, a 4-aminophenyl group, or a $C_1$-$C_4$ alkyl group, which is substituted with a nitrogen-containing group, a phenyl or a 4-aminophenyl group;

$G^2$ stands for a hydrogen atom, a $C_1$-$C_4$ alkyl group, a $C_1$-$C_4$ monohydroxyalkyl group, a $C_2$-$C_4$ polyhydroxyalkyl group, a $C_1$-$C_4$-alkoxy-($C_1$-$C_4$)-alkyl group, or a $C_1$-$C_4$ alkyl group, which is substituted with a nitrogen-containing group;

$G^3$ stands for a hydrogen atom, a halogen atom, such as a chlorine, bromine, iodine, or fluorine atom, a $C_1$-$C_4$ alkyl group, a $C_1$-$C_4$ monohydroxyalkyl group, a $C_2$-$C_4$ polyhydroxyalkyl group, a $C_1$-$C_4$ hydroxyalkoxy group, a $C_1$-$C_4$-alkoxy-($C_1$-$C_4$)-alkyl group, a $C_1$-$C_4$ acetylaminoalkoxy group, a mesylamino ($C_1$-$C_4$) alkoxy group, or a $C_1$-$C_4$ carbamoylaminoalkoxy group;

$G^4$ stands for a hydrogen atom, a halogen atom, a $C_1$-$C_4$ alkyl group, or a $C_1$-$C_4$-alkoxy-($C_1$-$C_4$)-alkyl group, or if $G^3$ and $G^4$ are in the ortho position to one another, they can together form a bridging α,ω-alkylenedioxo group such as, for example, an ethylenedioxy group.

Particularly preferred p-phenylenediamines of the formula (E1) are selected from one or more compounds from the group formed by p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis(2-hydroxyethyl)-p-phenylenediamine, 4-N,N-bis(2-hydroxyethyl)amino-2-methylaniline, 4-N,N-bis(2-hydroxyethyl)amino-2-chloroaniline, 2-(2-hydroxyethyl)-p-phenylenediamine, 2-(1,2-dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N,N-(ethyl, 2-hydroxyethyl-p-phenylenediamine, N-(2,3-dihydroxypropyl)-p-phenylenediamine, N-(4-aminophenyl)-p-phenylenediamine, N-phenyl-p-phenylenediamine, 2-(2-hydroxyethyloxy)-p-phenylenediamine, 2-methoxymethyl-p-phenylenediamine, 2-(2-acetylaminoethyloxy)-p-phenylenediamine, N-(2-methoxyethyl)-p-phenylenediamine, N-(4-amino-3-methylphenyl)-N-[3-(1H-imidazol-1-yl)propyl]amine, 5,8-diaminobenzo-1,4-dioxane, and the physiologically acceptable salts thereof. p-Phenylenediamine derivatives of the formula (E1), very especially preferred according to the invention, are selected from at least one compound from the group comprising p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, N-(4-amino-3-methylphenyl)-N-[3-(1H-imidazol-1-yl)propyl]amine, 2-methoxymethyl-p-phenylenediamine, and the physiologically acceptable salts thereof.

It can be preferable furthermore according to the invention to use as a developer component compounds that include at least two aromatic rings substituted with amino and/or hydroxyl groups.

Among bicyclic developer components that can be used in the dye compositions according to the invention, compounds can be named in particular that correspond to the following formula (E2) and the physiologically acceptable salts thereof,

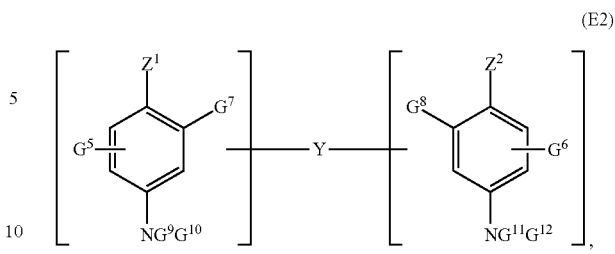

where $Z^1$ and $Z^2$ independently of one another stand for a hydroxyl or $NH_2$ group, which is optionally substituted by a $C_1$-$C_4$ alkyl group, by a $C_1$-$C_4$ hydroxyalkyl group, and/or by a bridge Y or which optionally is part of a bridging ring system, the bridge Y stands for an alkylene group having 1 to 14 carbon atoms, such as a linear or branched alkylene chain or an alkylene ring which can be interrupted or terminated by one or more nitrogen-containing groups and/or one or more heteroatoms, such as oxygen, sulfur, or nitrogen atoms, and may possibly be substituted by one or more hydroxyl or $C_1$-$C_8$ alkoxy groups, or for a direct bond, $G^5$ and $G^6$ independently of one another stand for a hydrogen or halogen atom, a $C_1$-$C_4$ alkyl group, a $C_1$-$C_4$ monohydroxyalkyl group, a $C_2$-$C_4$ polyhydroxyalkyl group, a $C_1$-$C_4$ aminoalkyl group, or a direct bond to bridge Y, $G^7$, $G^8$, $G^9$, $G^{10}$, $G^{11}$, and $G^{12}$ independently of one another stand for a hydrogen atom, a direct bond to bridge Y, or a $C_1$-$C_4$ alkyl group, with the proviso that the compounds of the formula (E2) include only one bridge Y per molecule.

Preferred bicyclic developer components of the formula (E2) are selected in particular from at least one of the following compounds: N,N'-bis(2-hydroxyethyl)-N,N'-bis(4-aminophenyl)-1,3-diaminopropan-2-ol, N,N'-bis(2-hydroxyethyl)-N,N'-bis(4-aminophenyl)ethylenediamine, N,N'-bis(4-aminophenyl)tetramethylenediamine, N,N'-bis(2-hydroxyethyl)-N,N'-bis(4-aminophenyl)tetramethylenediamine, N,N'-bis(4-(methylamino)phenyl)tetramethylenediamine, N,N'-diethyl-N,N'-bis(4-amino-3-methylphenyl)ethylenediamine, bis(2-hydroxy-5-aminophenyl)methane, N,N'-bis(4-aminophenyl)-1,4-diazacycloheptane, N,N'-bis(2-hydroxy-5-aminobenzyl)piperazine, N-(4-aminophenyl)-p-phenylenediamine, and 1,10-bis(2',5'-diaminophenyl)-1,4,7,10-tetraoxadecane, and the physiologically acceptable salts thereof. Very particularly preferred bicyclic developer components of the formula (E2) are selected from among N,N'-bis(2-hydroxyethyl)-N,N'-bis(4-aminophenyl)-1,3-diaminopropan-2-ol, bis(2-hydroxy-5-aminophenyl)methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, or one of the physiologically acceptable salts thereof.

It can be preferred furthermore according to the invention to use a p-aminophenol derivative or one of the physiologically acceptable salts thereof as a developer component. Particularly preferred are the p-aminophenol derivatives of the formula (E3),

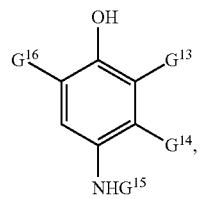

(E3)

where
- $G^{13}$ stands for a hydrogen atom, a halogen atom, a $C_1$-$C_4$ alkyl group, a $C_1$-$C_4$ monohydroxyalkyl group, a $C_2$-$C_4$ polyhydroxyalkyl group, a $C_1$-$C_4$-alkoxy-($C_1$-$C_4$)-alkyl group, a $C_1$-$C_4$ aminoalkyl group, a hydroxy-($C_1$-$C_4$)-alkylamino group, a $C_1$-$C_4$ hydroxyalkoxy group, a $C_1$-$C_4$-hydroxyalkyl-($C_1$-$C_4$)-aminoalkyl group, or a di-[($C_1$-$C_4$)-alkyl]amino-($C_1$-$C_4$)-alkyl group, and
- $G^{14}$ stands for a hydrogen or halogen atom, a $C_1$-$C_4$ alkyl group, a $C_1$-$C_4$ monohydroxyalkyl group, a $C_2$-$C_4$ polyhydroxyalkyl group, a $C_1$-$C_4$-alkoxy-($C_1$-$C_4$)-alkyl group, a $C_1$-$C_4$ aminoalkyl group, or a $C_1$-$C_4$ cyanoalkyl group,
- $G^{15}$ stands for hydrogen, a $C_1$-$C_4$ alkyl group, a $C_1$-$C_4$ monohydroxyalkyl group, a $C_2$-$C_4$ polyhydroxyalkyl group, a phenyl group, or a benzyl group, and
- $G^{16}$ stands for hydrogen or a halogen atom.

Preferred p-aminophenols of the formula (E3) are in particular p-aminophenol, N-methyl-p-aminophenol, 4-amino-3-methylphenol, 4-amino-3-fluorophenyl, 2-hydroxymethylamino-4-aminophenol, 4-amino-3-hydroxymethylphenol, 4-amino-2-(β-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(2-hydroxyethylaminomethyl)phenol, 4-amino-2-(1,2-dihydroxyethyl)phenol, 4-amino-2-fluorophenyl, 4-amino-2-chlorophenol, 4-amino-2,6-dichlorophenol, 4-amino-2-(diethylaminomethyl)phenol, and the physiologically acceptable salts thereof. Particularly preferred compounds of the formula (E3) are p-aminophenol, 4-amino-3-methylphenol, 4-amino-2-aminomethylphenol, 4-amino-2-(1,2-dihydroxyethyl)phenol, and 4-amino-2-(diethylaminomethyl)phenol. Further, the developer component can be selected from o-aminophenol and derivatives thereof, such as, for example, 2-amino-4-methylphenol, 2-amino-5-methylphenol, or 2-amino-4-chlorophenol. Furthermore, the developer component can be selected from heterocyclic developer components, such as, for example, pyrimidine derivatives, pyrazole derivatives, pyrazolopyrimidine derivatives, or the physiologically acceptable salts thereof. Particularly preferred pyrimidine derivatives are in particular the compounds: 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine, and 2,5,6-triaminopyrimidine. Particularly preferred pyrazole derivatives are in particular the compounds, selected from among 4,5-diamino-1-methylpyrazole, 4,5-diamino-1-(β-hydroxyethyl)pyrazole, 3,4-diaminopyrazole, 4, 5-diamino-1-(4-chlorobenzyl)pyrazole, 4,5-diamino-1,3-dimethylpyrazole, 4, 5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4, 5-diamino-1-ethyl-3-methylpyrazole, 4, 5-diamino-1-ethyl-3-(4-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole, and the physiologically acceptable salts thereof. Preferred pyrazolopyrimidines are pyrazolo[1,5-a]pyrimidines. Particularly preferred pyrazolo[1,5-a]pyrimidines are again pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5a]pyrimidin-3-yl)-(2-hydroxyethyl)amino]ethanol, 5,6-dimethylpyrazolo[1,5-a]pyrimidine-3,7-diamine, 2,6-dimethylpyrazolo[1, 5-a]pyrimidine-3,7-diamine, 3-amino-7-dimethylamino-2,5-dimethylpyrazolo[1,5-a]pyrimidine, and the physiologically acceptable salts thereof and the tautomeric forms thereof, if a tautomeric equilibrium exists.

Very particularly preferred developer components are selected from at least one compound from the group formed by p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, N-(4-amino-3-methylphenyl)-N-[3-(1H-imidazol-1-yl)propyl]amine, N,N'-bis(2-hydroxyethyl)-N,N'-bis(4-aminophenyl)-1,3-diaminopropan-2-ol, bis(2-hydroxy-5-aminophenyl)methane, 1,3-bis(2,5-diaminophenoxy)propan-2-ol, N,N'-bis(4-aminophenyl)-1,4-diazacycloheptane, 1,10-bis(2, 5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, and the physiologically acceptable salts thereof.

Preferred agents of the invention include at least one developer component in a total amount of 0.005 to 5 wt. %, preferably 0.1 to 3 wt. %, particularly preferably 0.5 to 2 wt. %, based in each case on the weight of the agent.

Coupler components during oxidative dyeing alone cause no significant coloring, but always require the presence of developer components. Therefore, it is preferred according to the invention that at least one developer component is used in addition when at least one coupler component is employed.

Coupler components in the context of the invention permit at least one substitution of a chemical group of the coupler by the oxidized form of the developer component. In this regard, a covalent bond forms between the coupler and developer component. Couplers are preferably cyclic compounds, which have at least two groups on the ring, selected from (i) optionally substituted amino groups and/or (ii) hydroxy groups. These groups are conjugated by a double-bond system.

Coupler components of the invention are preferably selected from the classes of m-aminophenol and/or derivatives thereof, m-diaminobenzene and/or derivatives thereof, o-diaminobenzene and/or derivatives thereof, naphthalene derivatives with at least one hydroxy group, di- or trihydroxybenzene and/or derivatives thereof, pyridine derivatives, pyrimidine derivatives, monohydroxyindole derivatives and/or monoaminoindole derivatives, monohydroxyindoline derivatives and/or monoaminoindoline derivatives, pyrazolone derivatives, such as 1-phenyl-3-methylpyrazol-5-one, morpholine derivatives, such as 6-hydroxybenzomorpholine or 6-aminobenzomorpholine, quinoxaline derivatives, such as 6-methyl-1,2,3,4-tetrahydroquinoxaline, and mixtures of two or more compounds from one or more of these classes.

Preferred m-aminophenol coupler components are selected from at least one compound from the group formed by m-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol, 2,4-dichloro-3-aminophenol, and the physiologically acceptable salts thereof. Preferred m-diaminobenzene coupler components are selected from at least one compound from the group formed by 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)-amino]ethanol, 3-amino-4-(2-methoxyethoxy)-5-methylphenylamine, 1-amino-3-bis(2'-hydroxyethyl)aminobenzene, and the physiologically acceptable salts thereof. Preferred o-diaminobenzene coupler components are selected from at least one compound from the group formed by 3,4-diaminobenzoic acid and 2,3-diamino-1-methylbenzene, and the physiologically acceptable salts thereof. Preferred di- or trihydroxybenzenes and derivatives thereof are selected from at least one compound from the group formed by resorcinol, resorcinol monomethyl ether, 2-methylresorcinol, 5-methylresorcinol, 2,5-dimethylresorcinol, 2-chlororesorcinol, 4-chlororesorcinol, pyrogallol, and 1,2,4-trihydroxybenzene. Preferred pyridine derivatives are selected from at least one compound from the group formed by 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 2, 6-dihydroxy-3,4-dimethylpyridine, 3,4-diaminopyridine, 2-(2-methoxyethyl)amino-3-amino-6-methoxypyridine, 2-(4'-methoxyphenyl)amino-3-aminopyridine, and the physiologically acceptable salts thereof. Preferred naphthalene derivatives with at least one hydroxy group are selected from at least one compound from the group formed by 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, and 2,3-dihydroxynaphthalene. Preferred indole derivatives are selected from at least one compound from the group formed by 4-hydroxyindole, 6-hydroxyindole, and 7-hydroxyindole, and the physiologically acceptable salts thereof. Preferred indoline derivatives are selected from at least one compound from the group formed by 4-hydroxyindoline, 6-hydroxyindoline, and 7-hydroxyindoline, and the physiologically acceptable salts thereof. Preferred pyrimidine derivatives are selected from at least one compound from the group formed by 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine, and the physiologically acceptable salts thereof.

Particularly preferred coupler components according to the invention are selected from among m-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol, 2,4-dichloro-3-aminophenol, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2-hydroxyethyl)aminobenzene, resorcinol, resorcinol monomethyl ether, 2-methylresorcinol, 5-methylresorcinol, 2,5-dimethylresorcinol, 2-chlororesorcinol, 4-chlororesorcinol, pyrogallol, 1,2,4-trihydroxybenzene, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 2,6-dihydroxy-3,4-dimethylpyridine, 3,4-diaminopyridine, 2-(2-methoxyethyl)amino-3-amino-6-methoxypyridine, 2-(4'-methoxyphenyl)amino-3-aminopyridine, 1-naphthol, 2-methyl-1-naphthol, 2-hydroxymethyl-1-naphthol, 2-hydroxyethyl-1-naphthol, 1,3-dihydroxynaphthalene, 1, 5-dihydroxynaphthalene, 1,6-dihydroxynaphthalene, 1,7-dihydroxynaphthalene, 1,8-dihydroxynaphthalene, 2,7-dihydroxynaphthalene, 2,3-dihydroxynaphthalene, 4-hydroxyindole, 6-hydroxyindole, 7-hydroxyindole, 4-hydroxyindoline, 6-hydroxyindoline, 7-hydroxyindoline, 4,6-diaminopyrimidine, 4-amino-2,6-dihydroxypyrimidine, 2,4-diamine-6-hydroxypyrimidine, 2,4, 6-trihydroxypyrimidine, 2-amino-4-methylpyrimidine, 2-amino-4-hydroxy-6-methylpyrimidine, and 4,6-dihydroxy-2-methylpyrimidine, or mixtures of said compounds or the physiologically acceptable salts thereof.

The coupler components are preferably present in a total amount of 0.005 to 20 wt. %, preferably 0.1 to 5 wt. %, particularly preferably 0.8 to 3 wt. %, based in each case on the agents of the invention.

In this case, the developer components and coupler components are generally used in approximately equimolar amounts to one another. Although the equimolar use has proven to be expedient, a certain excess of individual oxidation dye precursors is not disadvantageous, so that developer components and coupler components may have a molar ratio of 1:0.5 to 1:3, particularly 1:1 to 1:2.

In order to provide further nuances of the resulting color shades, it can be preferred according to the invention further to add at least one direct dye to the agent. These are dye molecules that are directly absorbed onto the substrate and do not require any oxidative process to develop the color. These dyes include, for example, henna which was already known in antiquity for dyeing skin and hair. Today direct dyes are usually nitrophenylenediamines, nitroaminophenols, azo dyes, anthraquinones, or indophenols.

The direct dyes are each preferably used in an amount of 0.001 to 10 wt. %, based in each case on the agent of the invention. The total amount of direct dyes is preferably at most 20 wt. %. Direct dyes can be divided into anionic, cationic, and nonionic direct dyes.

Preferred anionic direct dyes are the compounds known under the international names or trade names: Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, and Acid Black 52, as well as tetrabromophenol blue and bromophenol blue.

Preferred cationic direct dyes in this context are:
(a) cationic triphenylmethane dyes such as, for example, Basic Blue 7, Basic Blue 26, Basic Violet 2, and Basic Violet 14,
(b) aromatic systems substituted by a quaternary nitrogen group such as, for example, Basic Yellow 57, Basic Red 76, Basic Blue 99, Basic Brown 16, and Basic Brown 17, and
(c) direct dyes containing a heterocycle, which has at least one quaternary nitrogen atom, as specified, for example, in claims 6 to 11 in EP-A2-998 908, expressly incorporated here by reference. The compounds, which are also known under the names: Basic Yellow 87, Basic Orange 31, and Basic Red 51, are very particularly preferred cationic direct dyes.

The cationic direct dyes, which are marketed under the trademark Arianor$^{(R)}$, are cationic direct dyes, also very particularly preferred according to the invention.

Preferred nonionic direct dyes are compounds known under the international names or trade names: HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, and Disperse Black 9, and 1,4-diamino-2-nitrobenzene, 2-amino-4-nitrophenol, 1,4-bis(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl) amino-4-nitrobenzene, 2-[(4-amino-2-nitrophenyl)amino] benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Furthermore, naturally occurring dyes can also be used as direct dyes, as are found, for example, in henna red, henna neutral, henna black, chamomile blossoms, sandalwood, black tea, buckthorn bark, sage, logwood, madder root, catechu, and alkanna root.

A further subject matter of the present invention is a ready-to-use agent (also called an application mixture) for bleaching and/or dyeing keratinic fibers, consisting of a mixture of 25-75 wt. %, preferably 40 to 60 wt. %, particularly preferably 50 wt. %, based in each case on the weight of the application mixture, of an agent of the invention or preferred according to the invention with a pH in the range of 7.0 to 8.8, measured at 22° C., including
80-93 wt. %, based on the agent, of water or a mixture of water and at least one water-soluble polyol, whereby at least 30 wt. % of water, based on the agent, is present, furthermore
at least one hydrogel-forming polymer, selected from the group formed by polysaccharides, polymers and copolymers of acrylic acid, polymers and copolymers of methacrylic acid, and polymers and copolymers of 2-methyl-2[(1-oxo-2-propenyl)amino]-1-propanesulfonic acid, and of mixtures thereof, furthermore
at least one alkalizing agent, furthermore
at least one solubilizer, selected from fatty alcohol glycol ethers, fatty alcohols, fatty acid glycerol esters, and fatty acid sorbitan esters, each of which is ethoxylated and optionally propoxylated,
optionally at least one oxidation dye precursor and/or at least one direct dye,
and
75-25 wt. %, preferably 60 to 40 wt. %, particularly preferably 50 wt. %, based in each case on the weight of the application mixture, of an oxidizing agent preparation, including
75-95 wt. %, based on the weight of the oxidizing agent preparation, of water, or a mixture of water and at least one water-soluble polyol, preferably selected from at least one water-soluble polyhydric $C_2$-$C_9$ alkanol with 2-6 hydroxyl groups and/or at least one water-soluble polyethylene glycol with 3-20 ethylene oxide units, and mixtures thereof, particularly preferably selected from 1,2-propylene glycol, 1,3-propylene glycol, 2-methyl-1,3-propanediol, glycerol, 1,2-butylene glycol, 1,3-butylene glycol, 1,4-butylene glycol, 1,2-pentanediol, 1,5-pentanediol, 1,2-hexanediol, 1,6-hexanediol, 2-methyl-2,4-pentanediol, 1,2,6-hexanetriol, 1,2-octanediol, 1,8-octanediol, dipropylene glycol, tripropylene glycol, diglycerol, triglycerol, erythritol, sorbitol, cis-1,4-dimethylolcyclohexane, trans-1,4-dimethylolcyclohexane, any isomer mixtures of cis- and trans-1, 4-dimethylolcyclohexane, PEG-3, PEG-4, PEG-6, PEG-7, PEG-8, PEG-9, PEG-10, PEG-12, PEG-14, PEG-16, PEG-18, and PEG-20, as well as mixtures thereof, furthermore
at least one hydrogel-forming polymer, selected from the group formed by polysaccharides, polymers and copolymers of acrylic acid, polymers and copolymers of methacrylic acid, and polymers and copolymers of 2-methyl-2[(1-oxo-2-propenyl)amino]-1-propanesulfonic acid, and of mixtures thereof, furthermore
1.0 to 23.0 wt. % of hydrogen peroxide, based on the weight of the oxidizing agent preparation,
whereby the oxidizing agent preparation has a pH, in each case measured at 22° C., in the range of 2.0 to 6.5, preferably in the range of 3.0 to 4.5.

The statements made about the agents of the invention apply mutatis mutandis in regard to further preferred embodiments of the ready-to-use agent of the invention (also called an application mixture above).

The dyes in the oxidation dyes form first under the influence of an oxidizing agent; hydrogen peroxide is typically used for this purpose. In a preferred embodiment, hydrogen peroxide is used as an aqueous solution. Oxidizing agent preparations preferred according to the invention are characterized in that they include 1.0 to 23.0 wt. %, more preferably 2.5 to 21.0 wt. %, particularly preferably 4.0 to 20.0 wt. %, and very particularly preferably 5.0 to 18.0 wt.

% of hydrogen peroxide (calculated as 100% $H_2O_2$), based in each case on the weight of the oxidizing agent preparation.

It has proven advantageous, if the oxidizing agent preparations according to the invention include in addition at least one stabilizer or complexing agent for stabilizing the hydrogen peroxide. Especially preferred stabilizers are particularly EDTA, EDDS, and phosphonates, particularly 1-hydroxyethane-1,1-diphosphonate (HEDP), and/or ethylenediamine tetramethylene phosphonate (EDTMP), and/or diethylenetriamine pentamethylene phosphonate (DTPMP), or sodium salts thereof.

The at least one water-soluble polyol is preferably present in a total amount of 0.5-63 wt. %, particularly preferably in a total amount of 1-50 wt. %, more particularly preferably in a total amount of 2-30 wt. %, and exceedingly preferably in a total amount of 4-10 wt. %, based in each case on the weight of the oxidizing agent preparation.

The at least one hydrogel-forming polymer, selected from the group formed by polysaccharides, polymers and copolymers of acrylic acid, polymers and copolymers of methacrylic acid, and polymers and copolymers of 2-methyl-2[(1-oxo-2-propenyl)amino]-1-propanesulfonic acid, as well as of mixtures thereof, is preferably of the same kind and present in the same amount, as described above for the agent of the invention.

It is very particularly preferred, if the ready-to-use agent has a pH in the range of 6.0 to 7.3, preferably 6.2 to 6.9, in each case measured at 22° C. This pH, which is very low for an oxidative hair dye, contributes greatly to the reduction of hair damage. It can be preferable that the agent of the invention and/or the oxidizing agent preparation include at least one acid/base buffer substance. Preferred buffer substances are the phosphates, hydrogen phosphates, and dihydrogen phosphates of sodium and potassium. It is very particularly preferred, if the agent of the invention includes sodium phosphate, sodium hydrogen phosphate, sodium dihydrogen phosphate, potassium phosphate, potassium hydrogen phosphate, and/or potassium dihydrogen phosphate in a total amount of 0.1 to 1.0 wt. %, preferably 0.4 to 0.8 wt. %, based in each case on the weight of the agent of the invention.

A further subject matter of the present invention is a kit for dyeing and/or lightening keratinic fibers, comprising an agent according to one of claims 1 to 11 and an oxidizing agent preparation, including 75-93 wt. %, based on the weight of the oxidizing agent preparation, of water, or a mixture of water and at least one water-soluble polyol, preferably selected from at least one water-soluble polyhydric $C_2$-$C_9$ alkanol with 2-6 hydroxyl groups and/or at least one water-soluble polyethylene glycol with 3-20 ethylene oxide units, and mixtures thereof, particularly preferably selected from 1,2-propylene glycol, 1,3-propylene glycol, 2-methyl-1,3-propanediol, glycerol, 1,2-butylene glycol, 1,3-butylene glycol, 1,4-butylene glycol, 1,2-pentanediol, 1,5-pentanediol, 1,2-hexanediol, 1,6-hexanediol, 2-methyl-2,4-pentanediol, 1,2,6-hexanetriol, 1,2-octanediol, 1,8-octanediol, dipropylene glycol, tripropylene glycol, diglycerol, triglycerol, erythritol, sorbitol, cis-1,4-dimethylolcyclohexane, trans-1,4-dimethylolcyclohexane, any isomer mixture of cis- and trans-1,4-dimethylolcyclohexane, PEG-3, PEG-4, PEG-6, PEG-7, PEG-8, PEG-9, PEG-10, PEG-12, PEG-14, PEG-16, PEG-18, and PEG-20, as well as mixtures thereof, furthermore at least one hydrogel-forming polymer, selected from the group formed by polysaccharides, polymers and copolymers of acrylic acid, polymers and copolymers of methacrylic acid, and polymers and copolymers of 2-methyl-2[(1-oxo-2-propenyl)amino]-1-propanesulfonic acid, and of mixtures thereof, furthermore 1.0 to 23 wt. % of hydrogen peroxide, based on the weight of the oxidizing agent preparation, whereby the oxidizing agent preparation has a pH, in each case measured at 22° C., in the range of 2.0 to 6.5, preferably in the range of 3.0 to 4.5.

The statements made about the agents of the invention, the ready-to-use agents of the invention (therefore the application mixtures of the invention), and the oxidizing agent preparations to be used according to the invention apply mutatis mutandis in regard to further preferred embodiments of the kit of the invention.

A further subject matter of the present invention is a method for dyeing and/or lightening keratinic fibers, which comprises the following process steps:

optionally applying a pretreatment agent M1 to the fibers, then preparing and applying a ready-to-use agent M2 according to claim 12 or 13 to the fibers, rinsing off said agent M2 after a time period of 1 to 60 minutes from the fibers, and then optionally applying an aftertreatment agent M3 to the fiber and rinsing it off after a treatment time of 0.5 to 30 minutes.

The statements made about the agents of the invention and the oxidizing agent preparations used according to the invention apply mutatis mutandis in regard to other preferred embodiments of the method of the invention.

EXAMPLE

A dye gel of the invention, which has a pH (22° C.) of 8.2, is presented in the following table. (All quantities are given in wt. %, based on the agent of the invention)

| | |
|---|---|
| 1,2-Propylene glycol | 5.000000 |
| PPG-1-PEG-9 Lauryl Glycol Ether | 2.000000 |
| Toluene-2,5-diamine sulfate | 1.530000 |
| Xanthan gum | 1.000000 |
| Ethanolamine | 0.995000 |
| Carbomer | 0.800000 |
| PEG-12 dimethicone | 0.790000 |
| Potassium phosphate | 0.500000 |
| Perfume (fragrance) | 0.400000 |
| Sodium methylparaben | 0.390000 |
| 2-Methylresorcinol | 0.340000 |
| 2-Amino-3-hydroxypyridine | 0.312000 |
| 2-Amino-6-chloro-4-nitrophenol | 0.220000 |
| Citric acid | 0.200000 |
| Niacinamide | 0.150000 |
| Panthenol | 0.150000 |
| Sodium sulfite | 0.100000 |
| Ascorbic acid | 0.100000 |
| Polyquaternium-7 | 0.090000 |
| 4-Amino-2-hydroxytoluene | 0.072000 |
| PEG-14M | 0.070000 |
| m-Aminophenol | 0.069650 |
| Etidronic acid | 0.060000 |
| 4-Chlororesorcinol | 0.017000 |
| Aqua (water) | To 100.000 |

An oxidizing agent preparation used according to the invention, which has a pH (22° C.) of 4.0, is presented in the following table. (All quantities are given in wt. %, based on the oxidizing agent preparation used according to the invention).

| | |
|---|---|
| Hydrogen peroxide | 4.000000 |
| 1,2-Propylene glycol | 4.000000 |
| Xanthan gum | 2.000000 |
| Etidronic acid | 0.900000 |
| Sodium hydroxide | 0.328500 |
| 2,6-Dicarboxypyridine | 0.100000 |
| Disodium pyrophosphate | 0.030000 |
| Aqua (water) | To 100.000 |

The dye gel of the invention was mixed immediately before use with the previously described oxidizing agent preparation at room temperature in the weight ratio of 1:1 and intimately mixed. The thus obtained ready-to-use agent had a pH of 6.5 at 22° C. The ready-to-use agent was then applied to hair strands and rinsed out again after a treatment time of 30 minutes.

The strands were dried.

A conventional ready-to-use agent with a pH of 10.5 was tested in the same way.

A comparison of the cysteic acid value showed that the ready-to-use agent, not of the invention, with a pH of 10.5 produced a much higher cysteic acid value than the ready-to-use agent of the invention. The analysis of free cysteic acid provides a measure for hair damage (more cysteic acid is synonymous with greater hair damage).

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A kit for dyeing and/or lightening keratinic fibers, comprising:
    an agent for dying and/or lightening keratinic fibers, comprising:
        80-93 wt. %, based on the agent, of water or a mixture of water and at least one water-soluble polyol, whereby at least 30 wt. % of water, based on the agent, is present,
        at least one hydrogel-forming polymer, selected from the group consisting of polysaccharides, polymers and copolymers of acrylic acid, polymers and copolymers of methacrylic acid, and polymers and copolymers of 2-methyl-2[(1-oxo-2-propenyl)amino]-1-propanesulfonic acid, and of mixtures thereof, furthermore
        at least one alkalizing agent,
        at least one solubilizer, selected from the group consisting of fatty alcohol glycol ethers, fatty alcohols, fatty acid glycerol esters, and fatty acid sorbitan esters, each of which is ethoxylated and optionally propoxylated,
        optionally at least one oxidation dye precursor and/or at least one direct dye,
        whereby the agent has a pH in the range of 7.0 to 8.8, measured at 22° C.; and
    an oxidizing agent preparation, including
        75-93 wt. %, based on the weight of the oxidizing agent preparation, of water, or a mixture of water and at least one water-soluble polyol,
        at least one hydrogel-forming polymer, selected from the group consisting of polysaccharides, polymers and copolymers of acrylic acid, polymers and copolymers of methacrylic acid, and polymers and copolymers of 2-methyl-2[(1-oxo-2-propenyl)amino]-1-propanesulfonic acid, and of mixtures thereof,
        1.0 to 23 wt. % of hydrogen peroxide, based on the weight of the oxidizing agent preparation,
        whereby the oxidizing agent preparation has a pH, in each case measured at 22° C., in the range of 2.0 to 6.5.

2. The kit according to claim 1, wherein the agent for dying and/or lightening keratinic fibers includes no anionic surfactants, no cationic surfactants, and no fatty acid diethanolamides.

3. The kit according to claim 1, wherein the at least one water-soluble polyol in the agent for dying and/or lightening keratinic fibers is selected from the group consisting of at least one water-soluble polyhydric C2-C9 alkanol with 2-6 hydroxyl groups, at least one water-soluble polyethylene glycol with 3-20 ethylene oxide units, and mixtures thereof.

4. The kit according to claim 1, wherein the at least one water-soluble polyol in the agent for dying and/or lightening keratinic fibers is selected from the group consisting of: 1,2-propylene glycol, 1,3-propylene glycol, 2-methyl-1,3-propanediol, glycerol, 1,2-butylene glycol, 1,3-butylene glycol, 1,4-butylene glycol, 1,2-pentanediol, 1,5-pentanediol, 1,2-hexanediol, 1,6-hexanediol, 2-methyl-2,4-pentanediol, 1,2,6-hexanetriol, 1,2-octanediol, 1,8-octanediol, dipropylene glycol, tripropylene glycol, diglycerol, triglycerol, erythritol, sorbitol, cis-1,4-dimethylolcyclohexane, trans-1,4-dimethylolcyclohexane, any isomer mixtures of cis- and trans-1,4-dimethylolcyclohexane, PEG-3, PEG-4, PEG-6, PEG-7, PEG-8, PEG-9, PEG-10, PEG-12, PEG-14, PEG-16, PEG-18, and PEG-20, and mixtures thereof.

5. The kit according to claim 1, wherein the at least one polysaccharide the agent for dying and/or lightening keratinic fibers is selected from the group consisting of: xanthan gum, cellulose, cellulose ethers, primarily hydroxyalkyl celluloses, in particular hydroxypropyl cellulose, hydroxypropyl methylcellulose, hydroxyethyl cellulose, carboxymethylcellulose, hydroxybutylmethylcellulose, methylhydroxyethylcellulose, sclerotium gum, succinoglucans, polygalactomannans, guar-gums and locust bean gum and derivatives thereof.

6. The kit according to claim 1, wherein the at least one polysaccharide is selected from the group consisting of: hydroxypropyl guar, carboxymethyl hydroxypropyl guar, hydroxypropylmethyl guar, hydroxyethyl guar, carboxymethyl guar, pectins, agar, kappa-carrageenan, iota-carrageenan, tragacanth, gum arabic, karaya gum, tara gum, gellan gum, gelatin, casein, propylene glycol alginate, alginic acids and salts thereof, mixtures thereof.

7. The kit according to claim 1, wherein the at least one polymer or copolymer of acrylic acid and/or methacrylic acid and/or 2-methyl-2[(1-oxo-2-propenyl)amino]-1-propanesulfonic acid in the agent for dying and/or lightening keratinic fibers is selected from the group consisting of: crosslinked homopolymers of acrylic acid, crosslinked homopolymers of 2-methyl-2[(1-oxo-2-propenyl)amino]-1-propanesulfonic acid, crosslinked copolymers of methacrylic acid and C1-C4-alkyl acrylates, crosslinked copolymers of acrylic acid and C1-C4 alkyl methacrylates, crosslinked copolymers of 2-methyl-2[(1-oxo-2-propenyl)

amino]-1-propanesulfonic acid and acrylamide, crosslinked copolymers of 2-methyl-2[(1-oxo-2-propenyl)amino]-1-propanesulfonic acid and vinylpyrrolidone, crosslinked copolymers of 2-methyl-2[(1-oxo-2-propenyl)amino]-1-propanesulfonic acid and 2-hydroxyethyl acrylate, crosslinked copolymers of 2-methyl-2[(1-oxo-2-propenyl)amino]-1-propanesulfonic acid and acrylic acid, crosslinked copolymers of acrylic acid and C10-30 alkyl acrylates, crosslinked terpolymers and quaterpolymers of 2-methyl-2[(1-oxo-2-propenyl)amino]-1-propanesulfonic acid or acrylic acid or methacrylic acid, and mixtures of said polymers.

8. The kit according to claim 1, wherein the agent for dying and/or lightening keratinic fibers includes at least one polysaccharaide and at least one polymer.

9. The kit according to claim 1, wherein the agent for dying and/or lightening keratinic fibers includes xanthan gum and at least one crosslinked acrylic acid homopolymer.

10. The kit according to claim 1, wherein the at least one alkalizing agent in the agent for dying and/or lightening keratinic fibers is selected from ammonia and at least one alkanolamine.

11. The kit according to claim 1, wherein the alkalizing agent in the agent for dying and/or lightening keratinic fibers is selected from the group consisting of:

2-aminoethan-1-ol (monoethanolamine), 3-aminopropan-1-ol, 4-aminobutan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methylpropanol, 2-amino-2-methylbutanol, 3-amino-2-methylpropan-1-ol, 1-amino-2-methylpropan-2-ol, 3-aminopropane-1,2-diol, 2-amino-2-methylpropane-1,3-diol, 2-amino-2-ethyl-1,3-propanediol, N,N-dimethylethanolamine, triethanolamine, diethanolamine, and triisopropanolamine, and mixtures of the aforesaid substances.

12. The kit according to claim 1, wherein the at least one solubilizer in the agent for dying and/or lightening keratinic fibers is selected from the group consisting of: ethoxylated $C_8$-$C_{24}$ alkanols with 9-100 mol of ethylene oxide per mole, $C_8$-$C_{24}$ alkyl epoxide-ethylene glycol adducts, which are ethoxylated with 5-20 mol of ethylene oxide per mole and propoxylated with 1 mol of propylene oxide per mole, with 9-100 mol of ethylene oxide per mole of ethoxylated glycerol monoesters, diesters, or triesters of linear saturated and unsaturated $C_{12}$-$C_{30}$ carboxylic acids, which may be hydroxylated, ethoxylated $C_8$-$C_{24}$ carboxylic acids with 9-100 mol of ethylene oxide per mole, with 9-100 mol of ethylene oxide per mole of ethoxylated sorbitan monoesters of linear saturated and unsaturated $C_{12}$-$C_{30}$ carboxylic acids, which may be hydroxylated, and mixtures of the aforesaid substances.

13. The kit according to claim 1, wherein the at least one solubilizer in the agent for dying and/or lightening keratinic fibers is PPG-1-PEG-9 Lauryl Glycol Ether.

* * * * *